(12) United States Patent
Liu et al.

(10) Patent No.: US 8,921,554 B2
(45) Date of Patent: Dec. 30, 2014

(54) SUBSTITUTED 1,2-AZABORINE HETEROCYCLES

(75) Inventors: Shih-Yuan Liu, Chestnut Hill, MA (US); Ashley Lamm, Eugene, OR (US)

(73) Assignee: State of Oregon Acting by and Through the State Board of Higher Education on Behalf of the University of Oregon, Eugene, OR (US)

( * ) Notice: Subject to any disclaimer, the term of this patent is extended or adjusted under 35 U.S.C. 154(b) by 755 days.

(21) Appl. No.: 12/844,790

(22) Filed: Jul. 27, 2010

(65) Prior Publication Data

US 2011/0021735 A1 Jan. 27, 2011

Related U.S. Application Data

(60) Provisional application No. 61/228,883, filed on Jul. 27, 2009, provisional application No. 61/228,893, filed on Jul. 27, 2009, provisional application No. 61/301,475, filed on Feb. 4, 2010, provisional application No. 61/348,673, filed on May 26, 2010.

(51) Int. Cl.
*C07D 221/00* (2006.01)
*C07F 5/02* (2006.01)

(52) U.S. Cl.
CPC . *C07F 5/02* (2013.01); *Y02E 60/364* (2013.01)
USPC ............................................. 546/13

(58) Field of Classification Search
USPC ............................................. 546/13
See application file for complete search history.

(56) References Cited

U.S. PATENT DOCUMENTS

| | | |
|---|---|---|
| 2008/0112883 A1 | 5/2008 | Autrey et al. |
| 2010/0295032 A1 | 11/2010 | Kwong et al. |
| 2011/0021818 A1 | 1/2011 | Liu et al. |

FOREIGN PATENT DOCUMENTS

WO WO2008/076076 A1 6/2008

OTHER PUBLICATIONS

Abbey et al., "Crystal Clear Structural Evidence for Electron Delocalization in 1,2-Dihydro-1,2-azaborines," *J. Am. Chem. Soc.* 130:7250-7252, 2008. (published online May 14, 2008).
Ashe and Fang, "A Synthesis of Aromatic Five- and Six-Membered B—N Heterocycles via Ring Closing Metathesis," *Organic Letters* 2(14):2089-2091, 2000. (published online Jun. 7, 2000).
Ashe et al., "Synthesis of 1,2-Dihydro-1,2-azaborines and Their Conversion to Tricarbonyl Chromium and Molybdenum Complexes," *Organometallics* 20:5413-5418, 2001. (published online Nov. 1, 2001).
Ashe et al., "Synthesis and Coordination Chemistry of 3a,7a-Azaborindenyl, a New Isoelectronic Analogue of the Indenyl Ligand," *Organometallics* 21:4578-4580, 2002. (published online Oct. 3, 2002).
Ashe et al., "Aromatic Borataheterocycles: Surrogates for Cyclopentadienyl in Transition-Metal Complexes," *Organometallics* 28:4236-4248, 2009. (published online Jul. 6, 2009).
Bertolini et al., "Paracetamol: New Vistas of an Old Drug," *CNS Drug Reviews* 12(3-4):250-275, 2006.
Campbell et al., "Hydrogen Storage by Boron—Nitrogen Heterocycles: A Simple Route for Spent Fuel Regeneration," *J. Am. Chem. Soc.* 132:3289-3291, 2010. (published online Feb. 19, 2010).
Daly et al., "Microwave Spectrum, Structural Parameters, and Quadrupole Coupling for 1,2-Dihydro-1,2-azaborine," *J. Am. Chem. Soc.* 132:5501-5506, 2010. (published online Mar. 29, 2010).
Davies et al., "New Heteroaromatic Compounds. XXVI. Synthesis of Borazarenes," *Journal of the American Chemical Society* 89(24):6294-6297, 1967.
Dewar et al., "A Derivative of Borazarene," *J. Am. Chem. Soc.* 84(19):3782, Oct. 1962.
Fang et al., "Syntheses of Ring-Fused B—N Heteroaromatic Compounds," *Organometallics* 25:513-518, 2006. (published online Nov. 25, 2005).
Jaska et al., "Synthesis, Characterization, and Fluorescence Behavior of Twisted and Planar B2N2-Quaterphenyl Analogues," *Journal of Organic Chemistry* 72:5234-5243, 2007. (published online Jun. 12, 2007).
Lam and Liu, "How stable are 1,2-dihydro-1,2-azaborines toward water and oxygen?" *Molecular BioSystems* 5:1303-1305, 2009. (published online Aug. 10, 2009).
Liu et al., "Boron Mimetics: 1,2-Dihydro-1,2-azaborines Bind inside a Nonpolar Cavity of T4 Lysozyme," *Angew. Chem. Int. Ed.* 48:6817-6819, 2009. (published Aug. 17, 2009).
Liu, Mar. 19, 2009, presentation to DOE Hydrogen Program, Detroit, MI "Hydrogen Storage by Novel CBN Heterocycle Materials".
Marwitz et al., "Diversity through Isosterism: The Case of Boron-Substituted 1,2-Dihydro-1,2-azaborines," *Organic Letters* 9(23):4905-4908, 2007. (published online Oct. 18, 2007).
Marwitz et al., "A Hybrid Organic/Inorganic Benzene," *Angew. Chem. Int. Ed.* 48:973-977, 2009. (published online Dec. 22, 2008).
Marwitz et al., "BN benzonitrile: an electron-deficient 1,2-dihydro-1,2-azaborine featuring linkage isomerism," *Chem. Commun.* 46:779-781, 2010. (published online Nov. 25, 2009).
Matus et al., "Dehydrogenation Reactions of Cyclic $C_2B_2N_2H_{12}$ and $C_4BNH_{12}$ Isomers," *J. Phys. Chem. A* 114:2644-2654, 2010. (published online Jan. 29, 2010).
Pan et al., "1,2-Azaboratabenzene: A Heterocyclic π-Ligand with an Adjustable Basicity at Nitrogen," *Organometallics* 23:5626-5629, 2004. (published online Oct. 13, 2004).

(Continued)

Primary Examiner — Samantha Shterengarts
(74) Attorney, Agent, or Firm — Klarquist Sparkman LLP

(57) ABSTRACT

Aromatic heterocycles incorporating boron and nitrogen atoms, in particular, 1,2-azaborine compounds having the formula

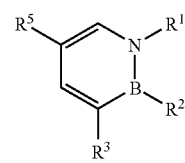

and their use as synthetic intermediates.

18 Claims, No Drawings

(56) References Cited

OTHER PUBLICATIONS

Pan et al., "Haptotropic Migration from the Six- to the Five-Membered Ring of (3a,7a-Azaborindenyl)tricarbonylchromium Anion," *Organometallics* 25:3463-3467, 2006. (published online Jun. 3, 2006).

Pan et al., "Switchable Haptotropic Migrations of Tricarbonylchromium Complexes of 1,2-Dihydro-2-phenyl-1,2-azaborine," *Organometallics* 25:197-202, 2006. (published online Dec. 3, 2005).

Pan et al., "Electrophilic Aromatic Substitution Reactions of 1,2-Dihydro-1,2- azaborines," *Organic Letters* 9(4):679-681, 2007. (published online Jan. 24, 2007).

Pan et al., "The Preparation and Crystal Structures of $\eta^1$-Derivatives of 2-Phenyl-1,2-azaboratabenzene," *Organometallics* 27:1345-1347, 2008. (published online Feb. 27, 2008).

Tanjaroon et al., "Microwave measurements and ab initio calculations of structural and electronic properties of N-Et-1,2-azaborine," *The Journal of Chemical Physics* 131:224312:224312-9, 2009. (published online Dec. 10, 2009).

White, "2-Phenyl-2,1-borazarene and Derivatives of 1,2-Azaboracycloalkanes," *Journal of the American Chemical Society* 85:3634-3636, 1963.

International Search Report and Written Opinion from International Application No. PCT/US2010/43444 dated Oct. 26, 2010.

International Search Report and Written Opinion from International Application No. PCT/US2010/43446 dated Nov. 23, 2010.

Marwitz et al., "1,2-Dihydro-1,2-azaborine: An Organometallic Benzene," *Dalton Discussion 11: The Renaissance of Main Group Chemistry*, Berkeley, CA (Poster Presentation) Jun. 24, 2008.

Office Action dated Jan. 9, 2013 for U.S. Appl. No. 12/844,797, 20 pages.

SUBSTITUTED 1,2-AZABORINE HETEROCYCLES

CROSS-REFERENCE TO RELATED APPLICATIONS

This applications claims the benefit under 35 U.S.C. §119(e) of the priority of U.S. Provisional Patent Application No. 61/228,883 titled 1,2-AZABORINE HETEROCYCLES filed Jul. 27, 2009; U.S. Provisional Patent Application No. 61/228,893 titled AZABORINE COMPOUNDS AS HYDROGEN STORAGE SUBSTRATES filed Jul. 27, 2009; U.S. Provisional Patent Application No. 61/301,475 titled AZABORINE ISOSTERES OF ACETAMINOPHEN AND L-DOPA filed Feb. 4, 2010; and U.S. Provisional Patent Application No. 61/348,673 titled SYNTHESIS AND MODIFICATION OF SELECTED BN-SUBSTITUTED HETEROCYCLES filed May 26, 2010, all hereby incorporated by reference.

As provided for by the terms of Grant No. DE-FG36-08GO18143 awarded by the Department of Energy, the U.S. Government has certain rights in the invention.

BACKGROUND

Heterocycles, or heterocyclic compounds, are cyclic organic compounds, either aromatic or nonaromatic, that have at least one non-carbon ring atom, typically sulfur, oxygen or nitrogen. Heterocyclic compounds often exhibit chemical reactivities distinct from that of their pure carbon analogs, and such compounds have been found to possess utility in a variety of industries including medicine, materials science, synthetic chemistry, and nanotechnology, among others. Heterocyclic analogs of benzene may be found to possess particularly advantageous properties.

SUMMARY

Aromatic heterocycles incorporating boron and nitrogen atoms are prepared. In particular, 1,2-azaborine compounds selectively substituted at one or more of the 1, 2, 3, 4, 5, and 6 positions are prepared.

DETAILED DESCRIPTION

The compounds of the present disclosure may be described by the following formula

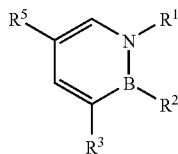

where the $R^1$ substituent is hydrogen, halogen, alkyl having 1-6 carbons, aryl having 1-6 carbons, heteroaryl having 1-6 carbons, acyl having 1-6 carbons, alkenyl having 1-6 carbons, alkynyl having 1-6 carbons, sulfonyl, —$OR^7$, an amine protecting group APG, or $Si(R^8)_3$. Each $R^7$ is independently hydrogen, alkyl having 1-6 carbons, acyl having 1-6 carbons, alkenyl having 1-6 carbons, tert-butyloxycarbonyl, or sulfonyl. Each $R^8$ is independently alkyl having 1-6 carbons, aryl having 1-6 carbons, alkoxy having 1-6 carbons, acyl having 1-6 carbons, alkenyl having 1-6 carbons, and tert-butyloxycarbonyl.

The $R^2$ substituent is hydrogen, halogen, —CN, acyl having 1-6 carbons, amide, alkenyl having 1-6 carbons, alkynyl having 1-6 carbons, aryl having 1-6 carbons, or $R^2$ is an aromatic heterocycle. Alternatively $R^1$ and $R^2$ taken in combination form a fused 5- or 6-membered ring that optionally incorporates one or more heteroatoms, and that is itself optionally further substituted by alkyl having 1-6 carbons, aryl having 1-6 carbons, acyl having 1-6 carbons, tert-butyloxycarbonyl or $Si(R^8)_3$. In yet another alternative, the $R^2$ moiety is a leaving group LG.

The $R^3$ substituent is hydrogen, halogen, alkyl having 1-6 carbons, acyl having 1-6 carbons, amide, alkenyl having 1-6 carbons, alkynyl having 1-6 carbons, —$OR^7$, —CN, thiol, $SR^7$, sulfonyl, aryl having 1-6 carbons, heteroaryl having 1-6 carbons, deuterium, or a leaving group LG.

The $R^5$ substituent is hydrogen, deuterium, halogen, alkyl having 1-6 carbons, acyl having 1-6 carbons, amide, alkenyl having 1-6 carbons, alkynyl having 1-6 carbons, —$OR^7$, hydroxyl, —CN, —$SR^7$, sulfonyl, aryl having 1-6 carbons, heteroaryl having 1-6 carbons, or a leaving group LG.

By "leaving group" (LG) is meant a functional group that is readily displaced or otherwise labile. That is, it may be readily displaced by an incoming reagent to form a new compound. A particular class of leaving groups is the "protecting group", a functional group or associated chemical moiety that protects a molecule or portion of a molecule from undesired reactions, but may be readily removed under the appropriate conditions (deprotection).

Typically a leaving group LG is displaced with a concomitant heterolytic cleavage of the bond to the LG. Preferred leaving groups include halides, diazonium salts, nonaflates, triflates, fluorosulfonates, tosylates, and mesylates, among others. Preferred leaving groups are tosylate, mesylate, —O-sulfonyl, and cyano.

The amine protecting group APG is a functional group bound to the amine that prevents the amine from taking part in any undesired reactions, but which can still be removed when desired. Typically amine protecting groups include carbobenzyloxy, p-methoxybenzyl carbonyl, tert-butyloxycarbonyl, 9-Fluorenylmethyloxycarbonyl, acetyl, benzoyl, benzyl, p-methoxybenzyl, 3,4-dimethoxybenzyl, p-methoxyphenyl, tosyl, and sulfonamide, among others.

In one embodiment, the $R^1$ moiety is alkyl, aryl, vinyl, acyl, BOC, or $Si(R^8)_3$; $R^2$ is Cl; $R^3$ is Br, Cl, F, OH, OTf, or $OR^7$; and $R^5$ is Br, Cl, F, OH, OTf, $OR^7$, where each $R^7$ and $R^8$ is as defined above.

In an alternative embodiment, the compounds of the disclosure have the formula

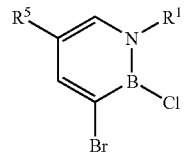

where the $R^1$ moiety may be hydrogen, deuterium, halogen, alkyl having 1-6 carbons, aryl having 1-carbons, heteroaryl having 1-6 carbons, acyl having 1-6 carbons, alkenyl having 1-6 carbons, alkynyl having 1-6 carbons, sulfonyl, —$OR^7$, an amine protecting group, or $Si(R^8)_3$. The $R^7$ substituent is hydrogen, alkyl having 1-6 carbons, acyl having 1-6 carbons, alkenyl having 1-6 carbons, tert-butyloxycarbonyl, or sulfonyl, and each $R^8$ is independently alkyl having 1-6 carbons, aryl having 1-6 carbons, alkoxy having 1-6 carbons, acyl having 1-6 carbons, alkenyl having 1-6 carbons, and tert-butyloxycarbonyl.

The $R^5$ moiety is hydrogen, deuterium, halogen, alkyl having 1-6 carbons, aryl having 1-carbons, heteroaryl having 1-6 carbons, acyl having 1-6 carbons, alkenyl having 1-6 carbons, alkynyl having 1-6 carbons, sulfonyl, —$OR^7$, an amine protecting group, or $Si(R^8)_3$, where $R^7$ and $R^8$ are as defined above. In one aspect of the disclosed compound, $R^5$ is iodide.

In one aspect of the above compound the $R^1$ moiety is alkyl having 1-6 carbons, preferably $R^1$ is tert-butyl.

In another aspect of the disclosed compounds, the azaborine has the formula

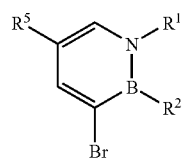

where the $R^1$ moiety is as defined above, and the $R^2$ substituent is an alkenyl or alkynyl moiety. The $R^5$ moiety is hydrogen, deuterium, halogen, alkyl having 1-6 carbons, aryl having 1-carbons, heteroaryl having 1-6 carbons, acyl having 1-6 carbons, alkenyl having 1-6 carbons, alkynyl having 1-6 carbons, sulfonyl, —$OR^7$, an amine protecting group, or $Si(R^8)_3$, where $R^7$ and $R^8$ are as defined above. IN one aspect of the compounds, $R^2$ is a vinyl moiety. In another aspect, $R^2$ is a penylacetylenyl moiety.

Selected compounds of the present disclosure may possess significant synthetic utility, in that a substituent at $R^3$ or $R^5$ that is readily displaced permits functionalization of the compound at that position. Furthermore, the $R^2$ substituent may also be selected to be particularly labile (i.e., a good leaving group) providing a synthetic route to additionally substituted 1,2-azaborine compounds. In particular, compounds having a diverse range of substituents at $R^1$, $R^2$, $R^3$, $R^4$, $R^5$, and $R^6$ may be readily prepared from the disclosed compounds. Such compounds are difficult or impossible to prepare using previously disclosed azaborine compounds.

In a further aspect of the disclosed compounds, the azaborine has the formula:

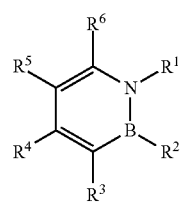

where $R^1$ is selected from alkyl having 1-6 carbons, aryl having 1-6 carbons, acyl having 1-6 carbons, tert-Butyloxycarbonyl (BOC), and $Si(R^7)_3$, where each $R^7$ is itself selected from alkyl having 1-6 carbons, aryl having 1-6 carbons, alkoxy having 1-6 carbons, acyl having 1-6 carbons, tert-Butyloxycarbonyl (BOC), and trialkylsilane, each alkyl independently having 1-6 carbons.

Substituent $R^2$ is Cl or OTf (triflate). Alternatively, substituents $R^1$ and $R^2$, taken in combination, form a fused 5- or 6-membered ring, optionally incorporating one or more heteroatoms, that is itself optionally further substituted by alkyl having 1-6 carbons, aryl having 1-6 carbons, acyl having 1-6 carbons, BOC, or $Si(R^7)_3$.

The 3-substituent $R^3$ is selected from H, Br, Cl, F, OH, OTf (triflate), OTs (tosylate), and $OR^7$, where $R^7$ is as described above.

Substituents $R^4$ and $R^6$ are selected from H, Br, Cl, F, OH, OTf, OTs, and $OR^7$, where $R^7$ is as described above.

Substituent $R^5$ is selected from H, Br, Cl, I, F, OH, OTf, OTs, and $OR^7$, where $R^7$ is as described above.

Where $R^1$ and $R^2$ form a fused ring structure, the ring structure may be a 5-membered nitrogen-containing heterocycle. In particular, $R^1$ and $R^2$ may be selected so as to form a compound that is an indole having the formula:

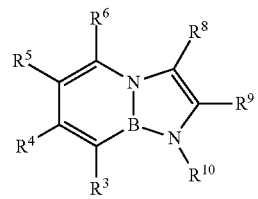

where $R^8$ and $R^9$ are independently selected from alkyl having 1-6 carbons, aryl having 1-6 carbons, acyl having 1-6 carbons, tert-Butyloxycarbonyl (BOC), and $Si(R^7)_3$, where $R^7$ is defined above. The N-substituent $R^{10}$ is selected from alkyl having 1-6 carbons, aryl having 1-6 carbons, acyl having 1-6 carbons, tert-Butyloxycarbonyl (BOC), and $Si(R^7)_3$, where each $R^7$ is defined above.

The compounds of the present disclosure possess synthetic utility, in that a Cl or Br substituent at $R^3$ permits functionalization of the compound at that position. Furthermore, the $R^2$ substituent may be selected to be particularly labile (i.e., a good leaving group) providing a synthetic route to additionally substituted 1,2-azaborine compounds. In particular, compounds having a diverse range of substituents at $R^1$, $R^2$, and $R^3$ may be readily prepared from the disclosed compounds. Such compounds would be difficult or impossible to prepare using previously disclosed azaborine compounds.

The following compounds represent individual exemplary embodiments of the compounds of this disclosure. While they may represent particularly advantageous compounds, they should not be considered to limit the scope of the disclosure.

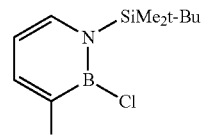 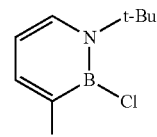

where X is Br or Cl;

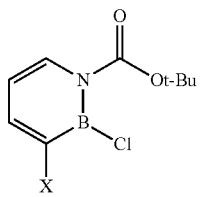 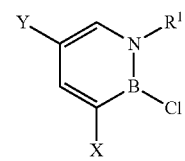

where $R^1$ is defined as above; X is Br, Cl, F, OH, OTf, OTs or $OR^5$; and Y is Br, Cl, F, OH, OTf, or $OR^5$; and

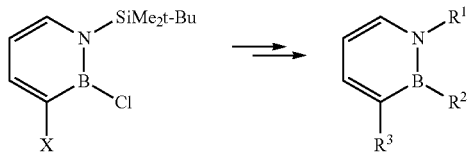

where $R^1 R^2$ and $R^3$ have been previously defined.

A general scheme for the preparation of 1,2-azaborines is shown below as Scheme 1A.

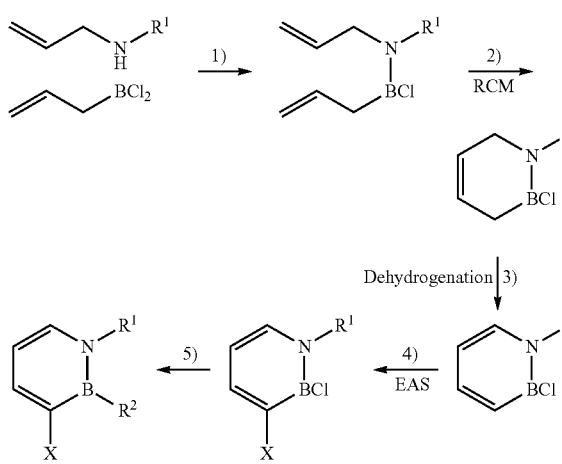

X = Br, Cl
RCM = ring closing metathesis
EAS = electrophilic aromatic substitution The synthetic strategy may include: 1) Condensation of an allyl amine and an allylboron dichloride that is generated in situ; 2) Ring-closing metathesis; 3) Dehydrogenation; 4) Electrophilic aromatic substitution; and 5) Nucleophilic displacement.

A particularly useful precursor to additional novel compounds may be described by the formula

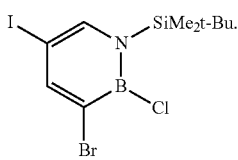

Compounds substituted at the boron atom by a facile leaving group, such as triflate (OTf) may exhibit enhanced electrophilicity at the boron atom, making them particularly useful in the preparation of novel 1,2-azaborine cation derivatives. The preparation has been accomplished using silver halide metathesis.

where $R^1$ is ethyl, t-butyl, or $SiMe_2(t\text{-}Bu)$.

Selected 1,2-azaborinium cation compounds display interesting photophysical properties, suggesting their use in new optoelectronic materials in materials and sensing applications.

As discussed above, the $R^1$ and $R^2$ substituents, taken in combination, may form a 5-membered ring, resulting in an azaborine analog of indole, for example

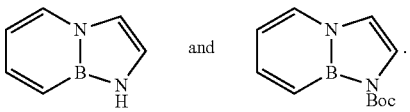 [SMILES: C1=CB2NC=CN2C=C1 ; CC(C)(C)OC(=O)N1C=CN2C=CC=CB21]

The members of the indole family of azaborines may be similarly substituted at any ring position, to yield the desired azaborine indole derivatives, including the following

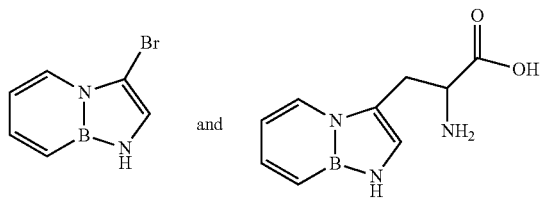

The compounds of the present disclosure represent a synthetic gateway to a large range of modified derivatives, including those that are substituted by leaving groups (LG), reactive functional groups (RF), or conjugated substances (CS).

By "leaving group" is meant a substituent or associated ion that is particularly labile. That is, it may be readily displaced by an incoming reagent to form a new compound. A particular class of leaving groups is the "protecting group", a functional group or associated chemical moiety that protects a molecule or portion of a molecule from undesired reactions, but may be readily removed under the appropriate conditions (deprotection).

By "reactive functional group" is meant a functional group capable of forming a covalent attachment with another molecule or substance. Reactive groups may vary in their reaction specificity, and are typically selected to possess the desired reactivity to form a covalent bond with a desired molecule or substance. A reactive group may be bound directly to the compound of the disclosure, or may be attached via some covalent spacer or linkage.

Reactive functional groups may be used to form conjugates of a substance of interest. Such conjugated substances may include for example amino acids, peptides, proteins, nucleosides, nucleotides, nucleic acids, or other biologically relevant substance. Alternatively, the conjugated substance may be a member of a specific binding pair.

A general scheme for the preparation of 1,2-azaborines is shown below as Scheme 1.

Scheme 1

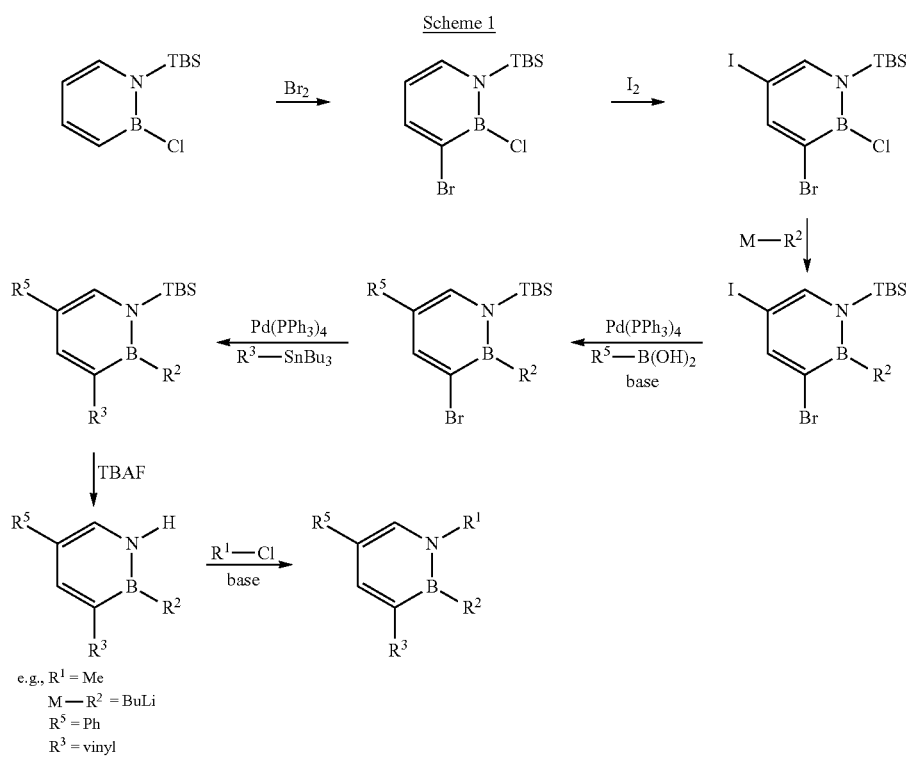

e.g., $R^1$ = Me
$M—R^2$ = BuLi
$R^5$ = Ph
$R^3$ = vinyl

This synthetic strategy may include: Treatment of the known (N-TBS, B—Cl) starting material with $Br_2$ to produce the C(3) brominated material through an electrophilic aromatic substitution (EAS) reaction. Subsequent treatment of this intermediate with $I_2$ generates the C(5) iodinated heterocycle also via an EAS reaction. This compound serves as a versatile intermediate to a variety of 1,2,3,5-substituted 1,2-azaborines. For instance, nucleophilic displacement of the B—Cl bond with a nucleophile (e.g., BuLi) installs a butyl group as the $R^2$ group. Subsequent Suzuki coupling introduces the $R^5$ substituent. The C(3) Br can then be further functionalized by for example a Stille reaction to install the C(3) substituent. Removal of the N-TBS group enables the introduction of the $R^1$ substituent by a substitution reaction.

In particular, the azaborine having the formula

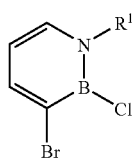

is a useful precursor for a variety of new azaborine compounds. Without wishing to be bound by theory, the presence of a halogen at the 2-position activates the position ortho to the halogen with respect to substitution reactions.

In particular, such a compound where $R^1$ is alkyl, aryl, vinyl, acyl BOO, or $Si(R^8)_3$ is preferred, particularly trialkylsilyl, useful, as each substituent then exhibits a distinct degree of reactivity, permitting selective substitution. In one aspect, $R^1$ is $SiMe_2$ t-Bu.

The following compounds represent individual exemplary embodiments of the compounds of this disclosure. While they may represent particularly advantageous compounds, they should not be considered to limit the scope of the disclosure.

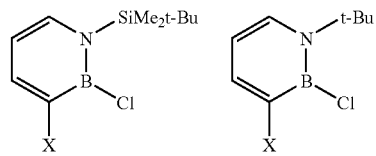

where X is Br or Cl;

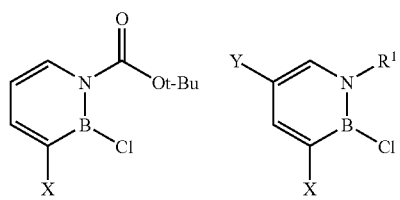

where $R^1$ is defined as above; X is Br, Cl, F, OH, OTf, OTs, or $OR^7$; and Y is I, Br, Cl, F, OH, OTf, or $OR^7$; and

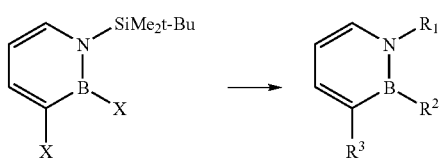

where $R^1$, $R^2$, $R^3$, $R^7$, and X have been previously defined.

A general scheme for the preparation of 1,2-azaborines is shown below as Scheme 2.

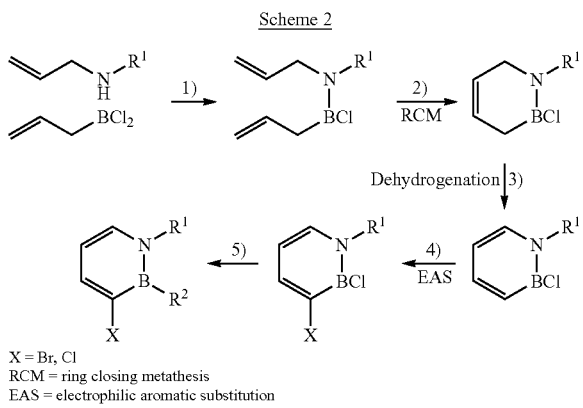

X = Br, Cl
RCM = ring closing metathesis
EAS = electrophilic aromatic substitution This synthetic strategy may include: 1) Condensation of a desired allyl amine and a desired allylboron dichloride that is generated in situ; 2) Ring-closing metathesis, for example in the presence of 2% first generation Grubbs catalyst; 3) Dehydrogenation of the resulting heterocycle, for example using palladium as a catalyst in the presence of a hydrogen acceptor; 4) Electrophilic aromatic substitution; and 5) Nucleophilic displacement. It should be appreciated that through careful selection of starting materials and nucleophilic agents a variety of desired compounds may be prepared.

A particularly useful precursor to additional novel compounds may be described by the formula:

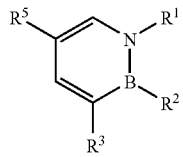

where one or more of $R^1$, $R^2$, $R^3$, and $R^5$ is selected to be readily displaced. A particular example where each of $R^1$, $R^2$, $R^3$, and $R^5$ is a replaceable moiety is

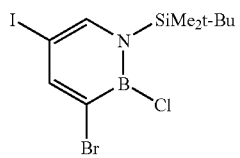

$R^1$ Displacement 1,2-azaborine compounds having a nonhydrogen substituent at $R^1$ provide a useful synthetic precursor for a variety of substituted 1,2-azaborine structures. A facile and cheap synthesis of such a compound would greatly simplify the preparation of azaborine analog compounds. To this end, Scheme 3 depicts a relatively inexpensive synthetic route to a compound substituted at the azaborine nitrogen by a labile protecting group (compound 1). Complexation of homoallylic amine 2 with $BH_3 \cdot THF$ produces 2. Intramolecular hydroboration of 2 occurs in toluene at elevated temperatures to furnish the cyclized BN heterocycle 3. Dehydrogenation of 3 produces the desired compound 1.

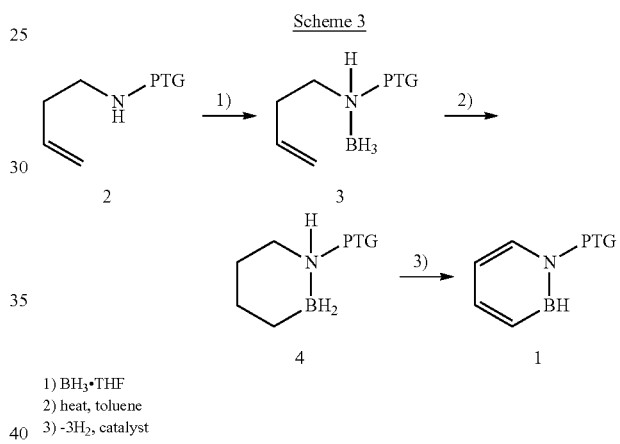

1) $BH_3 \cdot THF$
2) heat, toluene
3) $-3H_2$, catalyst

The compound 1, where the nonhydrogen substituent PTG at $R^1$ is TBS, may also be synthesized by the following route as depicted in Scheme 4.

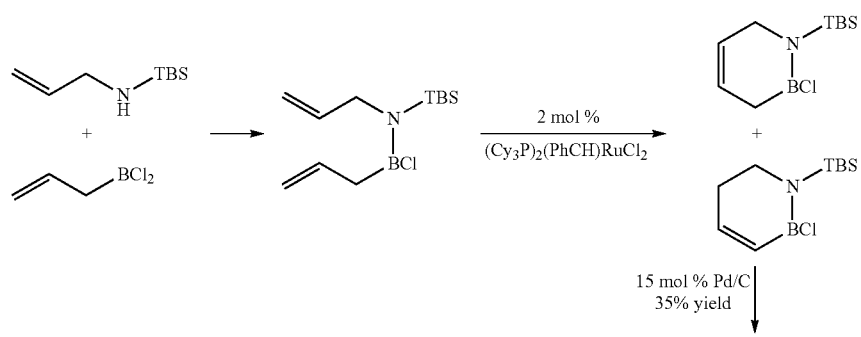

15 mol % Pd/C
35% yield

-continued

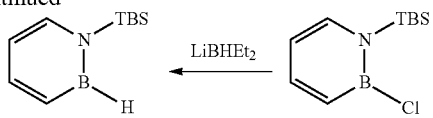

X = Br, Cl
RCM = ring closing metathesis
EAS = electrophilic aromatic substitution The compound 1, where the nonhydrogen substituent PTG at $R^1$ is t-Bu, may also be synthesized by the following route as depicted in Scheme 5. The known (N-TBS, B—Cl) starting material is treated with $LiBHEt_2$ to afford the 1,2-azaborine with a t-Butyl substituent at position 1 and where $R^2$-$R^6$ are hydrogens.

Scheme 5

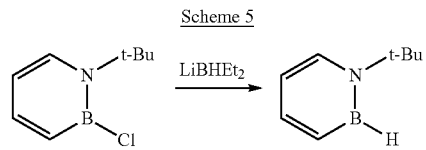

R² Displacement

Selected azaborine compounds that are substituted at the boron atom (substituent $R^2$) by a facile leaving group, such as triflate (OTf) among other, may exhibit enhanced electrophilicity at the boron atom, making them particularly useful in the preparation of novel cationic 1,2-azaborine derivatives. The preparation has been accomplished using silver halide metathesis as shown in Scheme 6:

Scheme 6

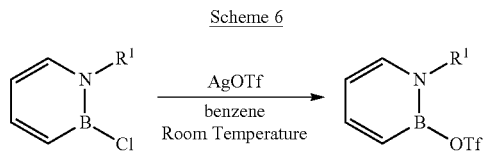

where $R^1$ is ethyl, t-butyl, or SiMe₂(t-Bu).

The reactivity of the compound 1,2-dihydro-1,2-azaborine (compound 5) has not previously been extensively explored due to the lack of practical synthetic methods for its preparation. The successful synthesis of compound 5 permits the preparation of a variety of azaborine derivatives via a variety of successful synthetic strategies, including a large selection of compounds that previously could not be made. We have recently succeeded in the preparation of 5 and investigated some of its properties.

For example, compound 5 readily undergoes nucleophilic aromatic substitution, a reactivity pattern that is not readily observed for the benzene molecule itself (see Scheme 7). Typically, the parent 1,2-dihydro-1,2-azaborine 5 is reacted with a nucleophile (Nu⁻) and quenched with an electrophile (E⁺) to give the substituted product 6.

Scheme 7

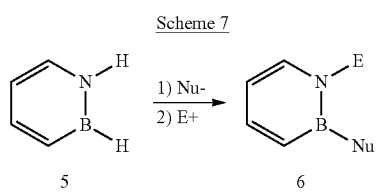

In a typical protocol, 5 is treated with two equivalents of a nucleophile (Nu–) followed by quenching with the desired electrophile (E+). A broad variety of appropriate nucleophiles and electrophiles may be used in the reaction, as shown in Table 1 below. Fore example, oxygen-based reagents including tert-butoxide, and allyloxide are suitable nucleophiles, producing the desired products in moderate to good yields. A variety of carbon nucleophiles also work very well. For instance sp³-, sp²-, and sp-hybridized carbon nucleophiles also generate the desired products efficiently. The reaction also seems to be independent of the steric demand of the nucleophile, as both the tert-butyl and n-butyllithium produced the desired adducts in good yield. The reaction is not restricted to organolithium reagents, as Grignard reagents are similarly effective. A variety of electrophiles, such as TMSCl, MeI and BnBr, among other, can also be used.

TABLE 1

Nucleophilic Aromatic Substitution of 1,2-Dihydro-1,2-Azaborine

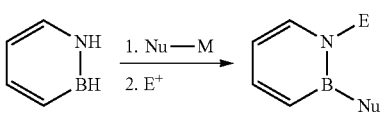

| Nu—M | E | Yield (%)[a] |
|---|---|---|
| Na—OtBu | H | 63 |
| K—Oallyl | H | 79 |
| Li—tBu | H | 81 |
| Li—nBu | H | 80 |
| Li—Ph | H | 98 |
| BrMg-vinyl | H | 59 |
| BrMg—≡—Ph | H | 71 |
| Li—nBu | TMS | 89 |
| Li—nBu | Me | 67 |
| Li—nBu | Bn | 60 |

[a]Isolated yield.

This discovery significantly expands the synthetic toolbox for 1,2-azaborine as it readily installs two substituents on the 1,2-azaborine nucleus in a one-pot reaction.

The method of preparing a substituted 1,2-azaborine, as described above, can be considered to include a) treating a starting 1,2-azaborine compound with a nucleophile Nu⁻ to generate an intermediate compound having a boron-Nu bond; and b) treating the intermediate compound with an electrophile E⁺ to generate a substituted 1,2-azaborine having a boron-Nu bond and a nitrogen-E bond. In one aspect of the method, the starting 1,2-azaborine compound is 1,2-dihydro-1,2-azaborine. Typically, the intermediate compound in the reaction is not isolated.

The nucleophile Nu⁻ is typically an oxygen-based nucleophile or a carbon-based nucleophile such as may be derived from an organolithium reagent or a Grignard reagent. The electrophile E⁺ may derived from an alkyl halide or silyl halide.

Analogs of Polypyridyl Compounds

In one embodiment, the disclosed azaborine compounds are substituted at $R^2$ by an aromatic heterocycle, which may in turn be substituted by another aromatic heterocycle. The resulting compounds can be considered to be azaborine analogs of bipyridyl and terpyridyl, respectively. Such compounds have been previously unavailable by conventional synthetic methods.

In one embodiment, the azaborine compounds have the formula

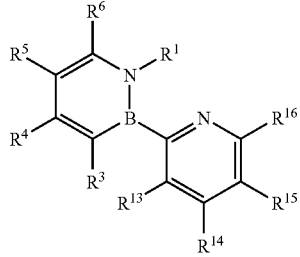

Wherein $R^1$ is hydrogen, deuterium, halogen, alkyl having 1-6 carbons, aryl having 1-carbons, heteroaryl having 1-6 carbons, acyl having 1-6 carbons, alkenyl having 1-6 carbons, alkynyl having 1-6 carbons, sulfonyl, —$OR^7$, an amine protecting group, or $Si(R^8)_3$, where $R^7$ is hydrogen, alkyl having 1-6 carbons, acyl having 1-6 carbons, alkenyl having 1-6 carbons, tert-butyloxycarbonyl, or sulfonyl, and each $R^8$ is independently alkyl having 1-6 carbons, aryl having 1-6 carbons, alkoxy having 1-6 carbons, acyl having 1-6 carbons, alkenyl having 1-6 carbons, and tert-butyloxycarbonyl.

Remaining substituents $R^3$-$R^6$ and $R^{13}$-$R^{15}$ are independently hydrogen, halogen, alkyl having 1-6 carbons, aryl, acyl having 1-6 carbons, amide, alkenyl having 1-6 carbons, alkynyl having 1-6 carbons, or a leaving group LG.

The $R^{16}$ substituent is hydrogen, halogen, alkyl having 1-6 carbons, aryl, acyl having 1-6 carbons, amide, alkenyl having 1-6 carbons, alkynyl having 1-6 carbons, or a leaving group LG; or $R^{16}$ is an aromatic or heteroaromatic ring system.

Where $R^{16}$ is an aromatic or heteroaromatic ring system, the resulting azaborine compound has the formula

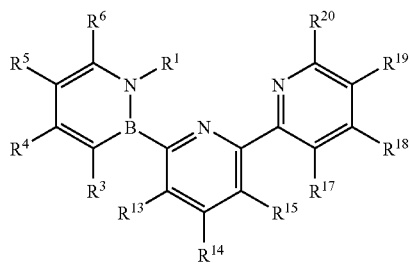

where substituents $R^{17}$-$R^{20}$ are independently hydrogen, halogen, alkyl having 1-6 carbons, aryl, acyl having 1-6 carbons, amide, alkenyl having 1-6 carbons, alkynyl having 1-6 carbons, or a leaving group LG.

A nonlimiting selection of examples of such bipyridyl and terpyridyl analogs is provided below:

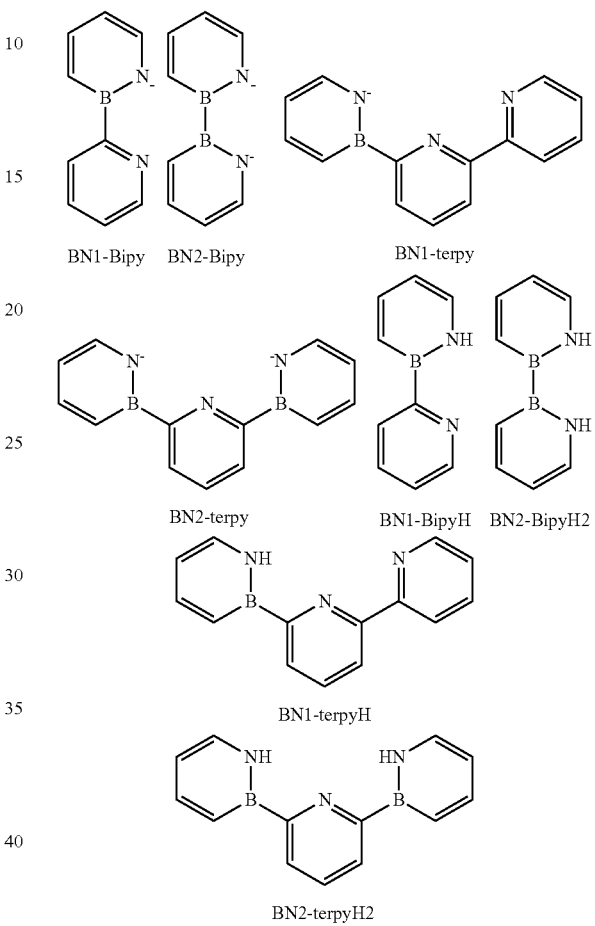

Through substitution of a C=C bond with the isoelectronic and isostructural inorganic B—N unit, 1,2-azaborine structures uniquely combine two important concepts in chemistry, i.e., aromaticity and BN/CC isosterism in one structural framework. As a result, the azaborine polypyridyls may provide new applications in materials science. In particular, 1,2-azaborines may be used as electronically distinct mimics of pyridine in solar energy conversion applications. We have found that the replacement of CC with BN in conjugated systems leads to materials with optoelectronic properties that are distinct from their analogous all-carbon systems. For example, substitution of BN for CC in such systems may lead to a significant red shift in the absorption spectrum and an enhancement in the molar absorptivity (c).

The synthetic route to azaborine-bipy ligands is shown below in Scheme 8. Treatment of the N-protected 1,2-azaborine precursor 7 with orthometallated pyridine results in heterocycle 8. Subsequent removal of the protecting group then yields the desired protonated azaborine bipy 9. Alternatively, the reaction of 7 with lithium metal in the presence of naphthalene ($C_{10}H_8$) generates the B—Li species 10. Reaction of 10 with another equivalent of starting material 10 furnishes the desired azaborine-bipyH$_2$ 11, which can then be deprotected to yield the desired compound.

A similar strategy can be employed for the synthesis of azaborine-terpy ligands as shown in Scheme 9 Treatment of 7 with the known ortho-lithiated bipy produces compound 12, which is then deprotected to yield the desired azaborine-terpyH 13.

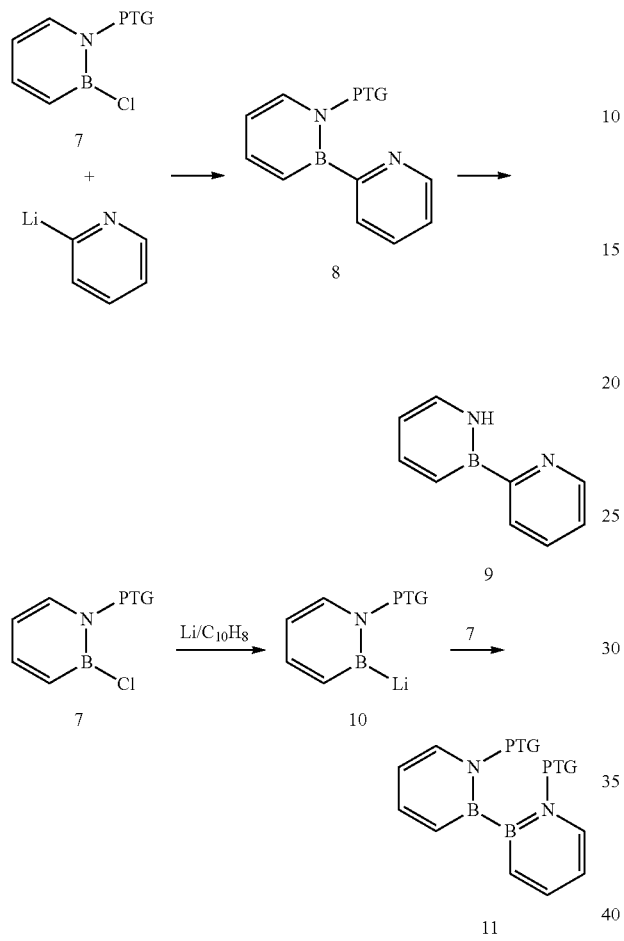

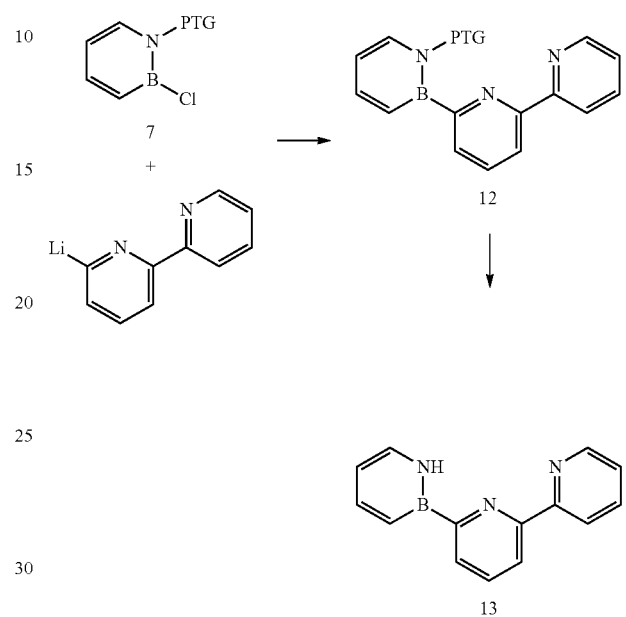

Alternatively, as shown in Scheme 10 precursor 7 may be reacted with bis-ortho-stannylated pyridine to give the bis-N-protected azaborine-terpy 14. Subsequent removal of the N-protecting groups furnishes the desired azaborine-terpyH$_2$ 15. Similarly, sequential treatment of 7 with ortholithiated bromopyridine produces 16, and metal-halogen exchange of this intermediate with Bu—Li gives the lithiated heterocycle 17. Reaction of 15 with precursor 7 yields 14. Deprotection then gives the desired azaborine-terpyH$_2$.

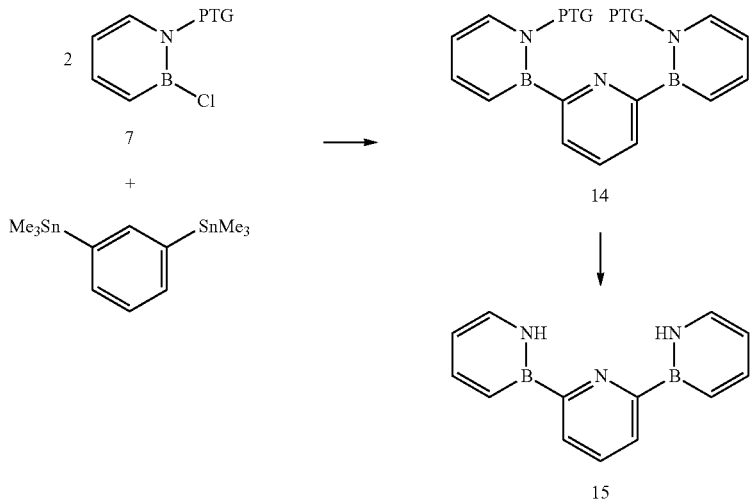

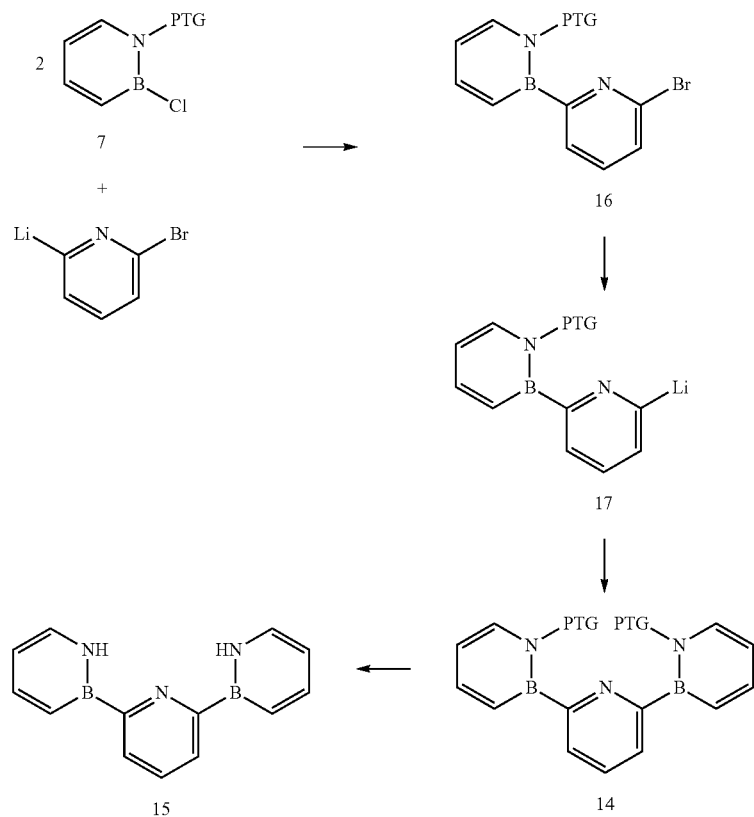

Of particular utility are the octahedral metal complexes formed by coordinating one, two, or three such azaborine polypyridine compounds (which may be the same or different) with at least one octahedral metal. By utilizing azaborine polypyridyls in place of conventional bipyridyl and terpyridyl as ligands in octahedral metal complexes, novel sensitizer dyes may be prepared and their properties investigated. For example, such compounds may have significant utility as components in solar energy conversion applications.

A selection of representative ruthenium complexes of azaborine polyridyl compounds are provided below (where SCN is thiocyanate). However, analogous complexes of metals such as Ir, Mo, Cr, Fe, Co, Mn, Rh, Os, Re, Al, Si, Eu, Tb, Gd, Ag, Cu, Ni, Zn, Tl, K, among others, may be readily envisioned and are accessible using synthetic techniques known in the art. Similarly, a variety of ligands other than thiocyanate may be used to occupy binding sites around the octahedral metal center.

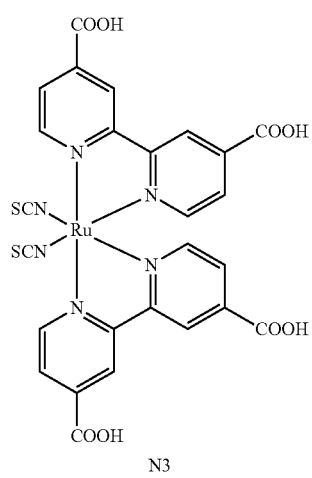

N3

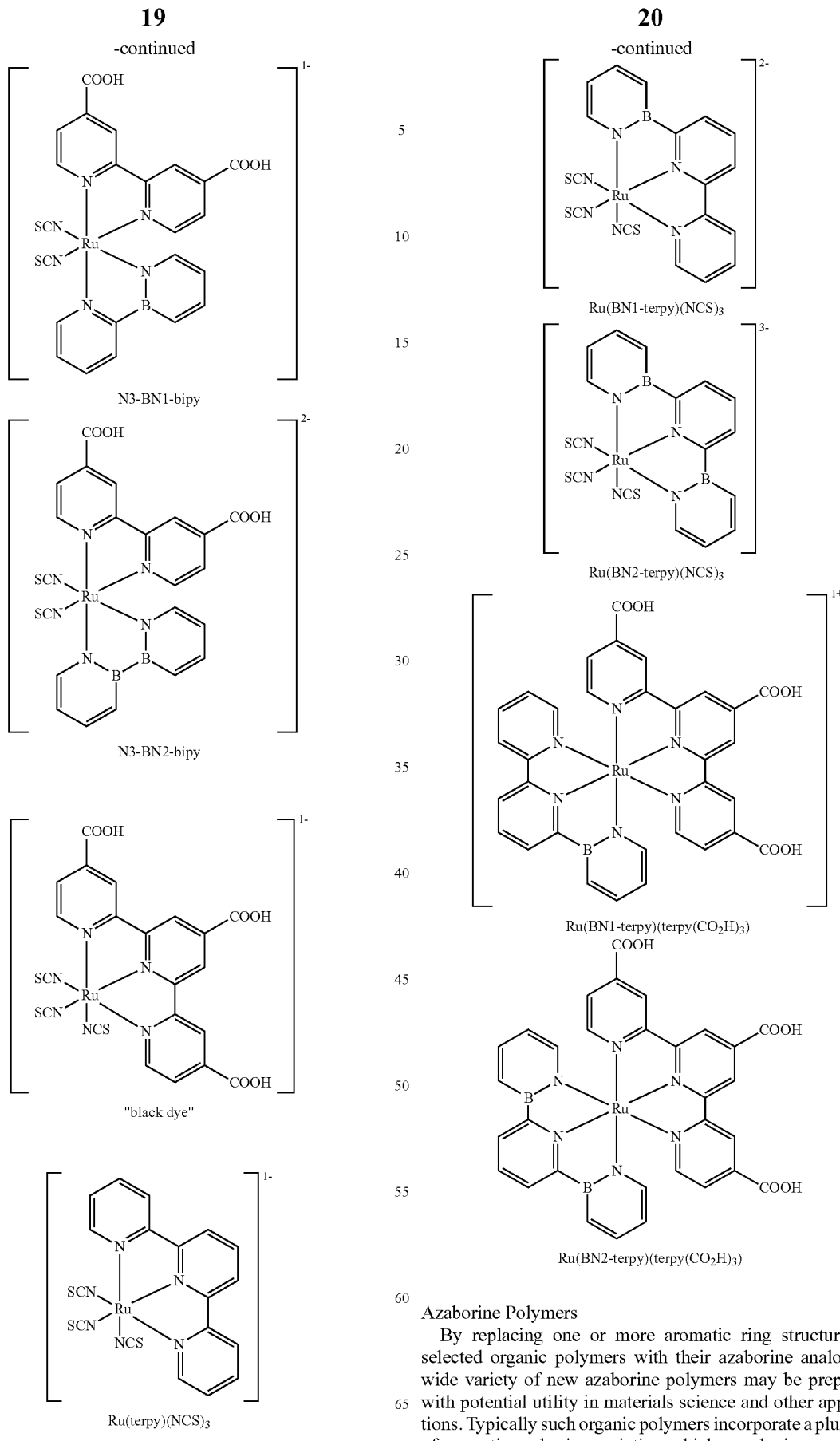

Azaborine Polymers

By replacing one or more aromatic ring structures in selected organic polymers with their azaborine analogs, a wide variety of new azaborine polymers may be prepared, with potential utility in materials science and other applications. Typically such organic polymers incorporate a plurality of aromatic azaborine moieties, which may be incorporated into the polymer backbone, or which may depend from the polymer backbone as pendant groups.

For example, via addition of an alkenyl substituent to the azaborine, an azaborine analog of styrene may be prepared, which may therefore be incorporated into members of the family of styrene-derived polymers (see Scheme 11).

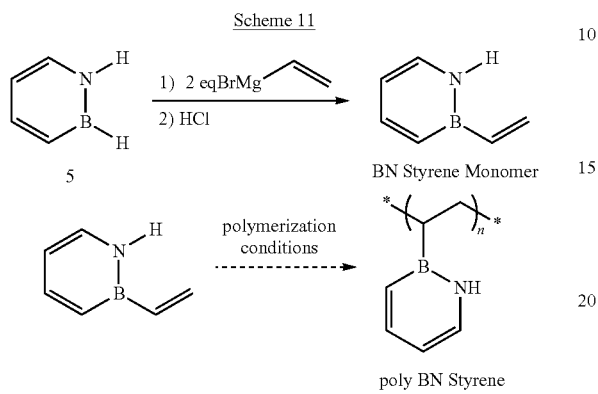

The synthesis of a BN-styrene may be accomplished using the parent 1,2-dihydro-1,2-azaborine (5) as the starting material. The addition of 2 equivalents of a vinyl magnesium Grignard reagent followed by quenching with HCl furnishes the desired BN-styrene in 60% yield (see Scheme 5).

The polymerization of BN-styrenes can be used to produce poly BN-styrene of a given molecular weight in a controlled fashion, using conventional polymerization techniques (e.g. anionic, radical, or cationic pathways using appropriate catalysts).

By replacing the aromatic heterocyclic rings in such polymers as polyaniline, polyaminopyridine, polymethylquinoline, polypyrrole, and polythiophene with a corresponding azaborine ring system, a novel family of polymeric solids may be prepared having applications as organic conductors for use in batteries, thin-layer displays, catalysis, anti-static and anti-corrosive materials, sensors, and gas separation membranes.

Similarly, azaborine analogs of fire-resistant polymers such as polyimides, polybenzoxazoles, polybnezimidazoles and polybenzthiazoles may offer polymers having improved properties. Where liquid crystal polymers incorporate aromatic rings, the substitution of azaborine in the polymer may result in similarly inert and fire-resistant polymers. Additionally, mixed polymers of azaborines and porphyrins, or other photoconductive azaborine polymers, may be useful as photorefractive materials.

Azaborine Polyphenyl Compounds

Given the structural similarity of arene and 1,2-azaborine discussed above, azaborine analogs of polyphenyl compounds may be prepared. These materials where selected C=C bonds are replaced with a BN bond pair may serve as novel scintillators, that is, molecules that exhibit luminescent emission when excited by ionizing radiation (e.g., $He^{2+}$, $Li^+$, γ-rays). Such high-energy particles are typically produced during a boron neutron capture reaction, and typical scintillator materials are aromatic compounds (e.g., terphenyl, quaterphenyl, POPOP, PPO etc). Selected azaborine analogs of such materials are illustrated below:

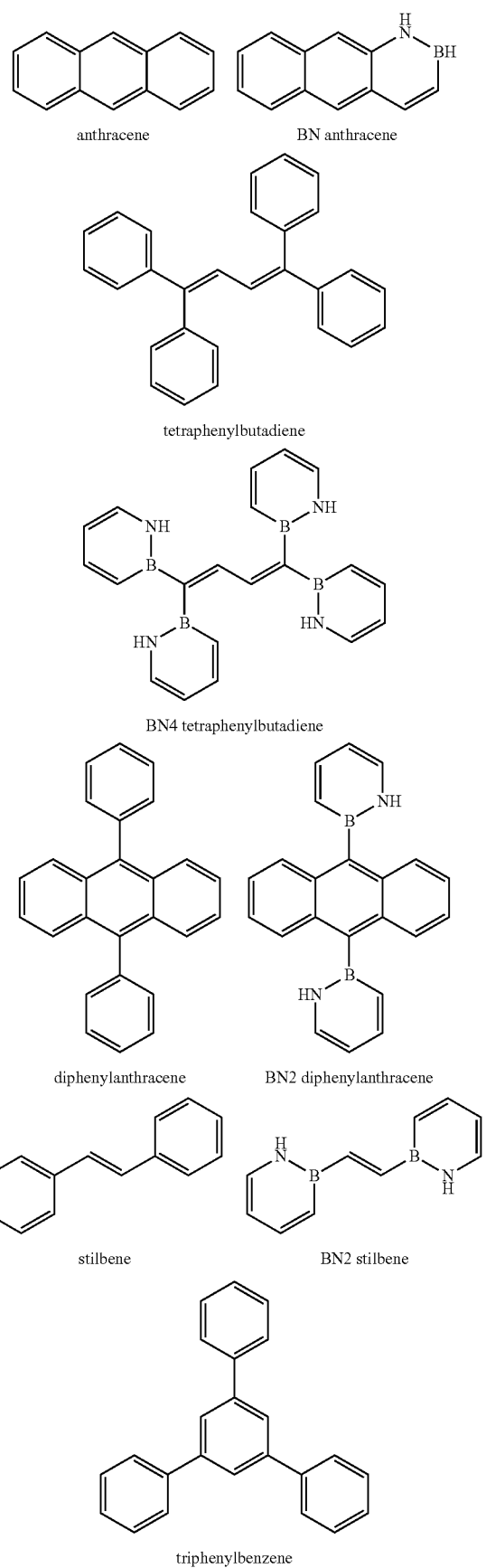

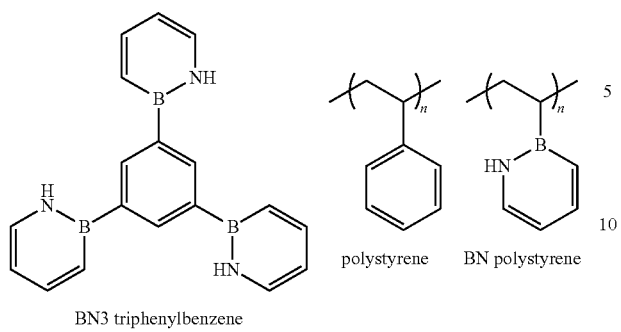

BN3 triphenylbenzene    polystyrene    BN polystyrene

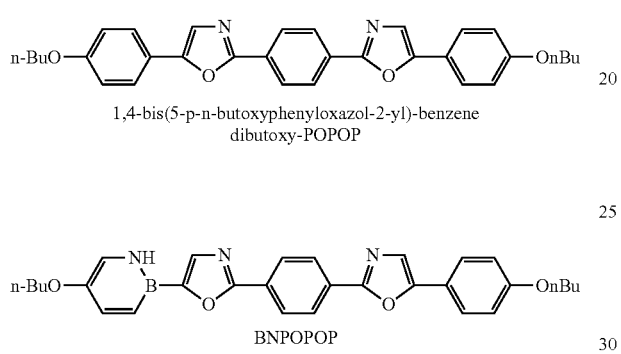

1,4-bis(5-p-n-butoxyphenyloxazol-2-yl)-benzene
dibutoxy-POPOP

BNPOPOP

Although the azaborine heterocycles materials disclosed herein are novel, their preparation may be accomplished using adaptations of synthetic methods previously reported in the literature. Azaborine anthracene may be synthesized from 3-vinyl-2-aminonaphthalene and boron trichloride (see Scheme 9). An alternative synthetic approach may be taken in the preparation of azaborine stilbene. The Liu group has established a versatile nucleophilic substitution protocol for the incorporation of the 1,2-azaborine motif into various structures via intermediate A (Scheme 12, eq. (2)). As a representative example, azaborine stilbene may be prepared using intermediate A and (E)-1,2-dibromoethene (after metal-halogen exchange) via the nucleophilic substitution approach. This general approach can be adapted to the synthesis of BN2 diphenylanthracene and BN3 triphenylbenzene. The Liu group has already accomplished the synthesis of a BN styrene monomer (R=Et, Scheme 9, eq (3), where R=ethyl). Polymerization of the monomer according to known methods furnishes the desired azaborine polystyrene.

Scheme 12

(1)

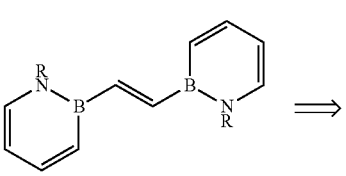

(2)

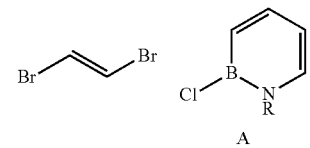

(3)

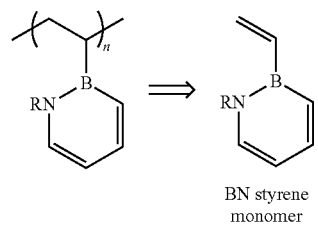

BN styrene monomer

A typical neutron-sensing device contains the following components:
(1) A material containing hydrogen to modulate fast neutrons;
(2) Boron-containing compounds to capture the modulated slow thermal neutrons; and
(3) Scintillators that capture the particles generated from the boron neutron capture reaction and produce a detectable response.

While the poly BN-styrene discussed above can serve as component (1) and/or (2) in such neutron sensing devices, the BN-polyphenyl scintillators may incorporate all three components (1)-(3) into a single material and may exhibit improved properties as compared to the current state of the art devices.

Azaborine Tolan Analogs

By combining azaborine substitution in phenyl moieties and elements of unsaturation in their substituents, organic materials exhibiting novel optical/electronic properties may be prepared. For example, azaborine analogs of diphenylacetylene (tolan) demonstrate the potential utility of such azaborine compounds.

In particular, the two tolan derivatives were prepared, tolan (1) and tolan(2), according to Schemes 13 and 14 below. The synthesis of tolan(1) begins with nucleophilic substitution of B-Clazaborine with phenylethynyl magnesium bromide furnished N-TBS protected compound 18 in 76% isolated yield. The reaction of 18 with $(MeCN)_3Cr(CO)_3$ gave the piano-stool complex 19 in 91% yield. Deprotection of the N-TBS group with HF-pyridine afforded the chromium tricarbonyl complex 20 in 85% yield. Simple dissolution of 20 in MeCN, followed by chromatographic purification gave 21 in good yield.

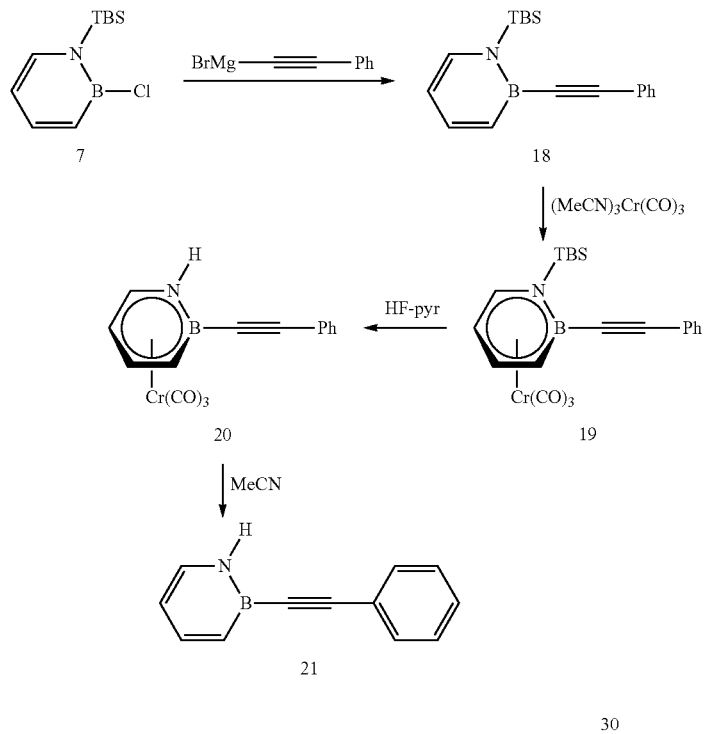
As shown in Scheme 14, in situ generation of Grignard reagent and reaction with 7 gave N-TBS protected compound 22 in good yield. The complexation of 22 with Cr(0) yielded complex 24 in 20% yield. N-TBS deprotection with HF-pyridine afforded 25 as a highly-insoluble orange solid, which was dissolved directly in MeCN to yield compound 26 (47%, two steps).
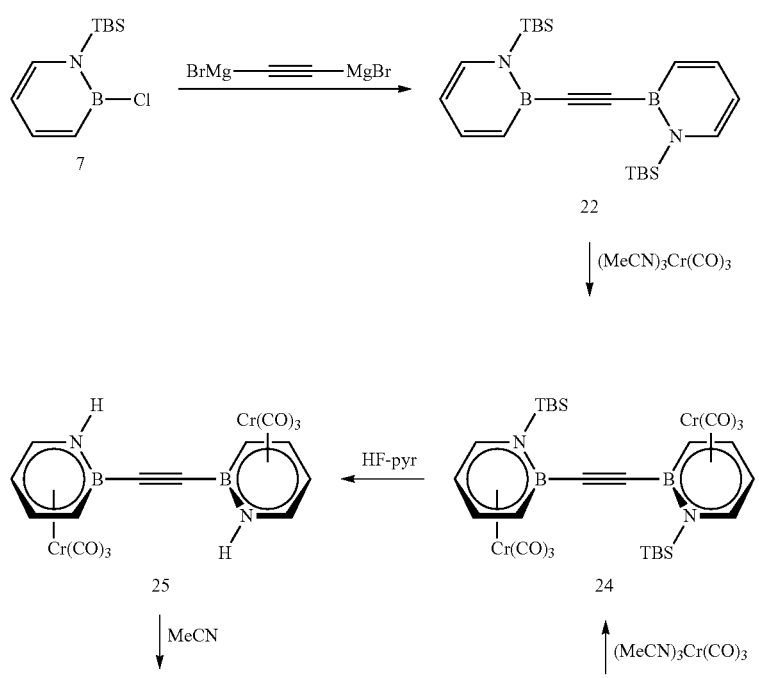

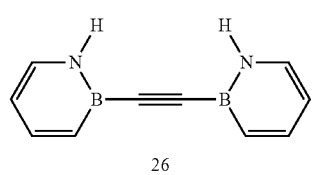

26

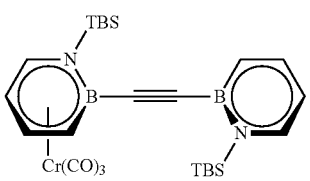

23

The azaborine tolan analogs both exhibit a red shift in emission spectra, as well as a significant increase in fluorescence quantum yield, relative to the original (carbonaceous) tolan compound. These enhanced photophysical properties, suggesting a variety of uses for azaborine compounds in new optoelectronic materials in materials and sensing applications.

Biomedical Applications

Azaborine-containing pharmaceuticals may prove highly beneficial, as boron's electrophilic character and unique bonding properties should lead to new mechanisms of biological activity that are not attainable by carbon-based compounds; 2) these novel pathways to interfere with targeted pathogens and boron's low "recognition" by mother nature should reduce the development of drug resistance. At the very minimum, the development of boron-based pharmaceuticals should widen the angles of attack against malignant organisms.

In addition, it is thought that boron's ability to form strong covalent bonds with hydroxyl groups may produce advantageous physiological effects. For instance, the proposed mechanism by which AN2690® exerts its antifungal activity is formation of strong inhibitory boron-oxygen bonds with the pathogen's Aminoacyl-transfer RNA (tRNA) synthetase. Specifically, the boron atom in AN2690 binds to the 2'- and 3'-oxygen atoms of leucyltRNA's 3'-terminal adenosine in the editing site of the enzyme, ultimately blocking the synthesis of proteins that are essential for the survival of the pathogen. Similarly, the family of diazaborines, six-membered heterocycles bearing two nitrogen and a boron, has been shown to exhibit antibacterial properties against Gram-negative bacteria. Their mechanism of action is thought to involve inhibition of NAD(P)H-dependent enoyl acyl carrier protein reductase (ENR), which ultimately prevents the synthesis of lipopolysaccharides—essential outer membrane ingredients of Gram-negative bacteria. X Ray structural analysis of a number of E. coli ENR-NAD+-diazaborine complexes revealed covalent bonding between the boron atom and the 2'-hydroxyl of the nicotinamide ribose in the active site The azaborine isostere of the medication STRATTERA can be prepared via the nucleophilic aromatic substitution. STRATTERA is a selective norepinephrine reuptake inhibitor used in the treatment of ADHD.

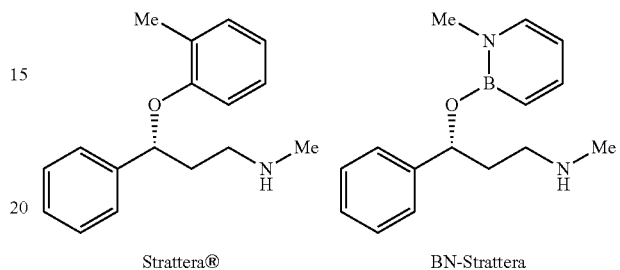

Strattera®  BN-Strattera

Indoles are one of the most ubiquitous heterocycles in Nature. Indole and its derivatives play pivotal roles in chemistry and biology. As discussed above, the $R^1$ and $R^2$ substituents, taken in combination, may form a 5-membered ring, resulting in an azaborine analog of indole, as exemplified below:

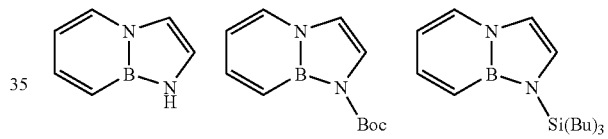

The members of the indole family of azaborines may be similarly substituted at any ring position, to yield the desired azaborine indole derivative. For example but not limited to the following:

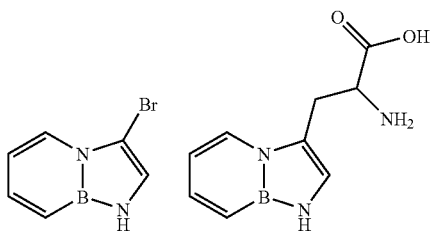

Important natural indoles include tryptamines, melatonin, and serotonin, which act as vital elements in brain function, as well as auxin, a ubiquitous plant hormone that regulates gene expression associated with plant growth. 5,6-Dihydroxyindole serves as a universal precursor for natural pigments, and it is implicated in malignant melanoma. Natural indole alkaloids have been exploited for the treatment of a variety of human diseases. Currently in clinical use are anticancer agents vinblastine and vincristine, the antimigraine drug ergotamine, and the antiarrythmic ajmalicine. Because of the rich chemistry and biological activity of indole-containing natural products, chemists have been attracted to synthesis and study of non-natural indole derivatives. Synthetic variants of indole natural products have found wide-ranging applications as pharmaceuticals (e.g., iprindole, pindolol, and indomethacin). A special natural indole derivative is the gene-encoded amino acid tryptophan. It is the biological precursor to the majority of aforementioned indole natural products.

The exploration of azaborine analogs of such biologically active compounds may offer insights into metabolism or mechanisms of action of a myriad of biological processes. Potential benefits of research into boron-based drugs include discovery of novel boron-specific mechanisms of biological activity that are unattainable by conventional organic molecules and attenuated development of drug resistance by targeted pathogens.

An exemplary synthesis of a BN-indole compound is shown in Scheme 15.

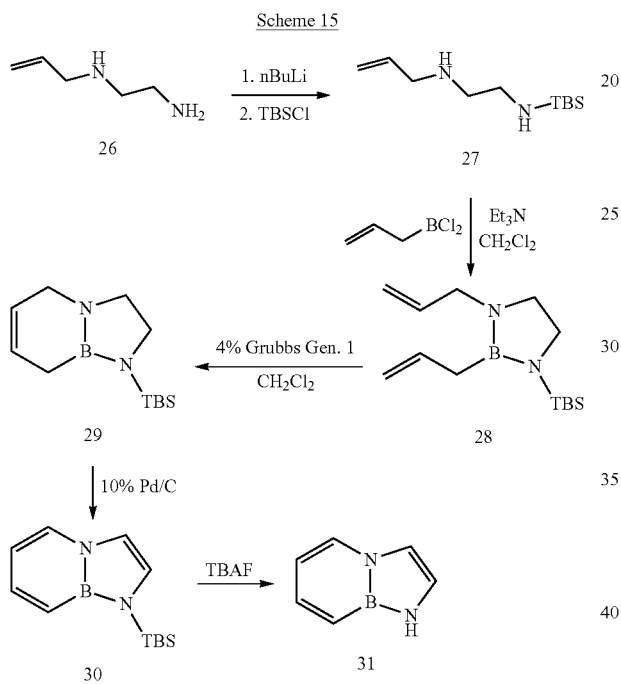

The BN-indole synthesis commences with the selective installation of a TBS group on the terminal nitrogen atom in diamine 26 using butyllithium and TBSCl. The resulting diamine 27 can then be reacted with the in-situ generated allylborondichloride to furnish diene 28. A ring-closing metathesis of 28 with Grubbs first generation catalyst produces 29, which can be dehydrogenated in the presence of Pd/C at high temperatures to yield the N-TBS protected BN-indole. Removal of the TBS protecting group with TBAF furnishes the desired BN-indole in a five-step synthetic sequence.

L-DOPA (L-3,4-dihydroxyphenylalanine) is a naturally-occurring dietary supplement and psychoactive drug found in certain kinds of food and herbs, and is synthesized in the mammalian body and brain from the essential amino acids L-phenylalanine (PHE) and L-tyrosine (TYR). L-DOPA is the precursor to the neurotransmitters dopamine, norepinephrine (noradrenaline), and epinephrine (adrenaline) collectively known as catecholamines. Aside from its natural and essential biological role, L-DOPA is also used in the clinical treatment of Parkinson's disease (PD) and dopamine-responsive dystonia (DRD).

L-DOPA is an electron rich arene which can form quinones upon oxidation. The toxic effects of L-DOPA may be related to these quinones and their formation may be avoided by azaborine analogs of the compound.

Several distinct azaborine analogs of L-DOPA may be prepared, as shown below. These analogs may be further substituted, as desired, at various positions.

BN L-DOPA Compounds

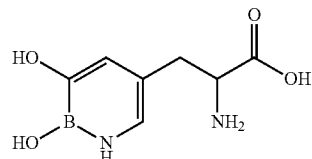

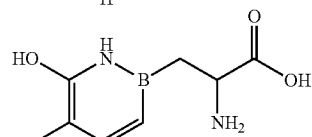

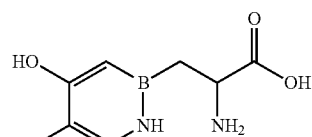

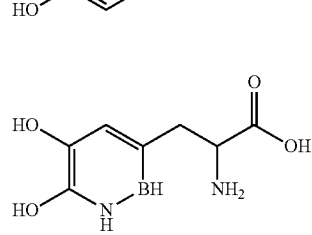

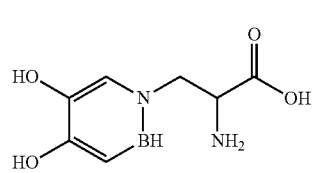

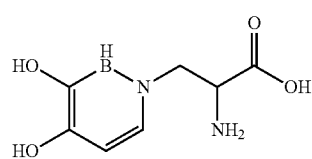

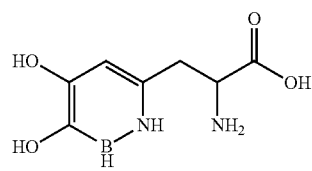

Acetaminophen (Tylenol) is a commonly used drug against fever and pain. Overdose and drug abuse can lead to severe liver toxicity. The metabolic intermediate responsible for toxicity of acetaminophen is N-acetyl-p-benzoquinoneimine, which is produced in the liver after oxidative metabolism (Scheme 16). N-acetyl-p-benzoquinoneimine is a reactive electrophilic species which can irreversibly bind and arylate critical cell proteins, therefore causing cell damage.

Scheme 16

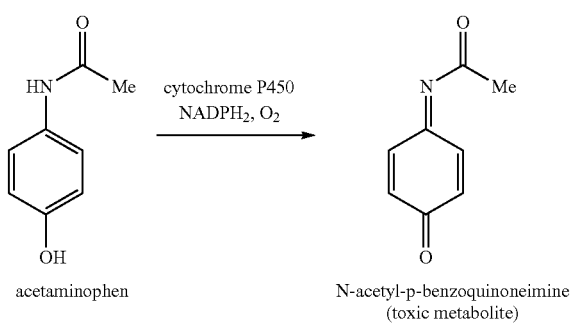

acetaminophen → N-acetyl-p-benzoquinoneimine (toxic metabolite)

An azaborine acetaminophen isostere may provide similar pharmacological properties as acetaminophen, while also eliminating the possibility of the formation of the toxic quinoidal intermediate (Scheme 17).

Scheme 17

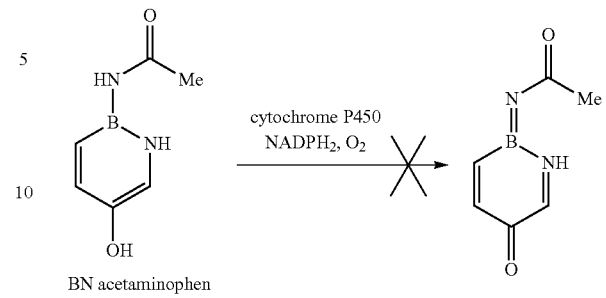

BN acetaminophen

Similar to L-DOPA, a variety of boron-nitrogen containing analogs of acetaminophen may be envisioned:

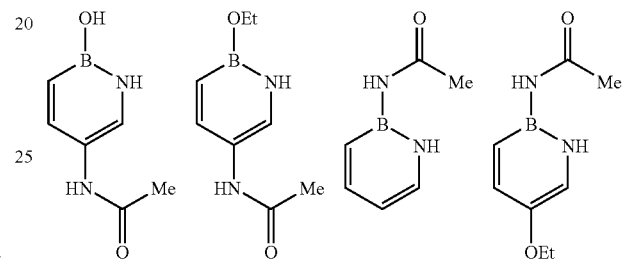

An exemplary synthesis of an azaborine analog of acetaminophen is given below as Scheme 18:

Scheme 18

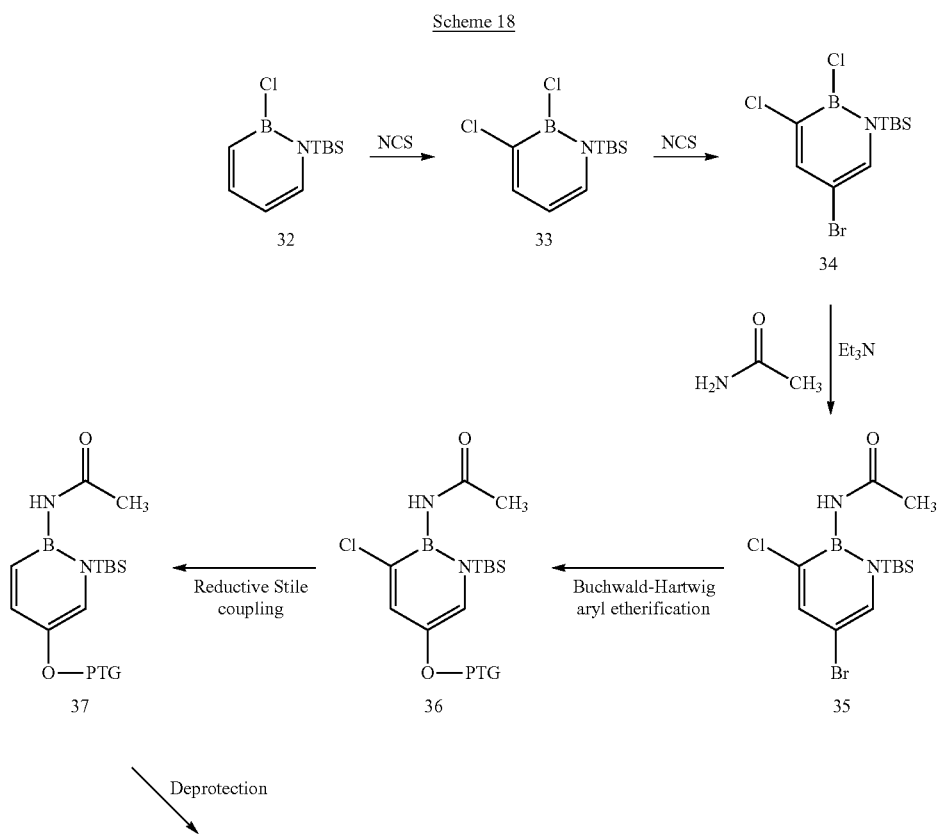

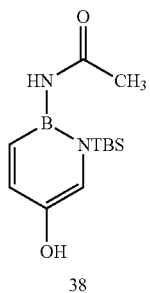

Alternatively, by taking advantage of nucleophilic aromatic substitution on 1,2-dihydro-1,2-azaborine, an alternative route to the azaborine acetaminophen can be formulated (see Scheme 19).

Scheme 19

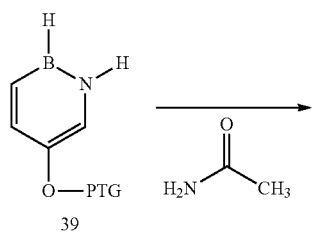

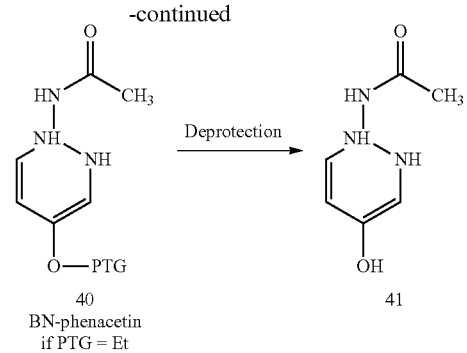

Treatment of 1,2-azaborine 39 with deprotonated acetamide produces compound 40. Removal of the protecting group (PTG) in 40 furnishes the desired BN acetaminophen. If the PTG group in 41 is an ethyl group the compound is analogous to phenacetin, another important member of the family of aniline analgesics.

Scheme 20 depicts a retrosynthetic analysis of 39, which involves ring-closing metathesis of 44 with subsequent dehydrogenation to form 42 as key steps. Alternatively, compound 39 can also be produced from the halogenated precursor 45. Halogenated 1,2-Azaborine 45 can be synthesized again using a ring-closing metathesis-dehydrogenation sequence starting from compound 48.

Scheme 20

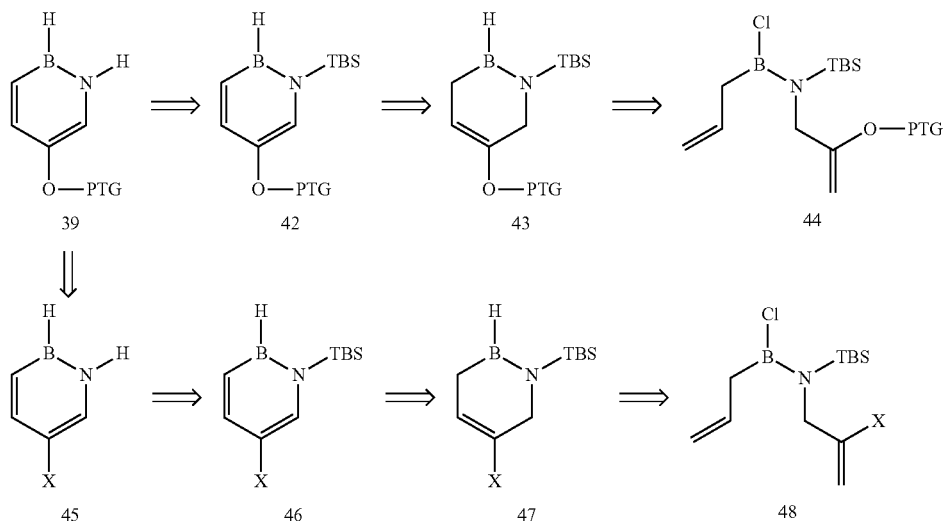

1,2-Azaborine 39 can also serve as a precursor toward an isomer of the targeted BN acetaminophen. Scheme 21 illustrates that treatment of 36 with Na—OMe should lead to 40. Subsequent Buchwald-Hartwig amination using acetamide as a substrate furnishes 41, an isomeric derivative of BN acetaminophen.

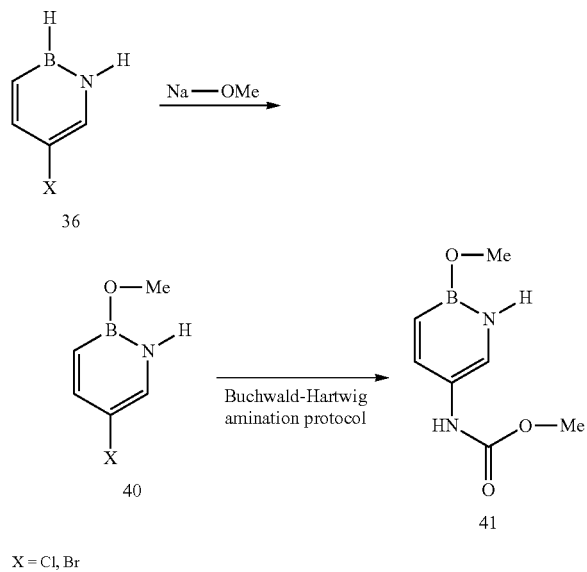

The treatment of 1,2-dihydro-1,2-azaborine with deprotonated acetamide provides an azaborine acetanilide (BN acetanilide, a member of the aniline analgesics) as shown in Scheme 22.

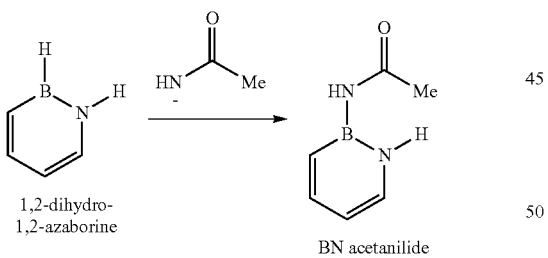

Selected alternative azaborine substituted anesthetics are provided below:

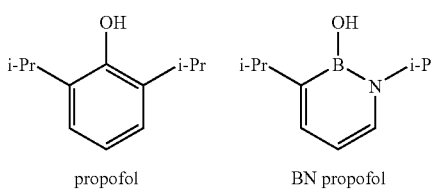

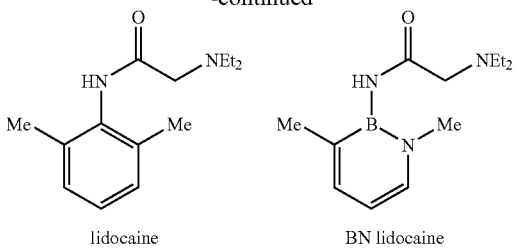

The compounds of the present disclosure represent a synthetic gateway to a large range of modified derivatives, including those that are substituted by leaving groups (LG), reactive functional groups (RF), or conjugated substances (CS).

By "reactive functional group" is meant a functional group capable of forming a covalent attachment with another molecule or substance. Reactive groups may vary in their reaction specificity, and are typically selected to possess the desired reactivity to form a covalent bond with a desired molecule or substance. A reactive group may be bound directly to the compound of the disclosure, or may be attached via some covalent spacer or linkage.

Reactive functional groups may be used to form conjugates of a substance of interest. Such conjugated substances may include for example amino acids, peptides, proteins, nucleosides, nucleotides, nucleic acids, or other biologically relevant substance. Alternatively, the conjugated substance may be a member of a specific binding pair.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

What is claimed is:
1. An azaborine having the formula

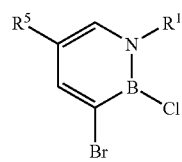

wherein $R^1$ is hydrogen, deuterium, halogen, alkyl having 1-6 carbons, aryl having 1-carbons, heteroaryl having 1-6 carbons, acyl having 1-6 carbons, alkenyl having 1-6 carbons, alkynyl having 1-6 carbons, sulfonyl, —$OR^7$, an amine protecting group, or $Si(R^8)_3$, where each $R^7$ is independently hydrogen, alkyl having 1-6 carbons, acyl having 1-6 carbons, alkenyl having 1-6 carbons, tert-butyloxycarbonyl, or sulfonyl, and each $R^8$ is independently alkyl having 1-6 carbons, aryl having 1-6 carbons, alkoxy having 1-6 carbons, acyl having 1-6 carbons, alkenyl having 1-6 carbons, or tert-butyloxycarbonyl;

$R^5$ is hydrogen, deuterium, halogen, alkyl having 1-6 carbons, acyl having 1-6 carbons, amide, alkenyl having 1-6 carbons, alkynyl having 1-6 carbons, —$OR^7$, hydroxyl, —CN, —$SR^7$, sulfonyl, aryl having 1-6 carbons, heteroaryl having 1-6 carbons, or a leaving group LG.

2. The azaborine of claim 1, wherein $R^1$ is alkyl having 1-6 carbons.
3. The azaborine of claim 1, wherein $R^1$ is tert-butyl.
4. The azaborine of claim 1, wherein $R^1$ is $Si(R^8)_3$.
5. The azaborine of claim 4, wherein $R^1$ is —$SiMe_2$t-Bu.
6. The azaborine of claim 1, wherein $R^5$ is a halogen.
7. The azaborine of claim 1, wherein $R^5$ is hydrogen.
8. The azaborine of claim 1, wherein $R^5$ is I, Br, Cl, F, OH, OTf or $OR^7$.
9. The azaborine of claim 1, wherein $R^1$ is alkyl, aryl, vinyl, acyl, BOC, or $Si(R^8)_3$.
10. The azaborine of claim 1, wherein $R^1$ is —$SiMe_2$t-Bu and $R^5$ is Br.
11. The azaborine of claim 1, wherein $R^5$ is Br.
12. The azaborine of claim 4, wherein $R^5$ is a halogen.
13. The azaborine of claim 9, wherein $R^5$ is I, Br, Cl, F, OH, OTf or $OR^7$.
14. The azaborine of claim 7, wherein $R^1$ is alkyl, aryl, vinyl, acyl, BOC, or $Si(R^8)_3$.
15. The azaborine of claim 1, wherein $R^1$ is tert-butyl.
16. An azaborine having the formula

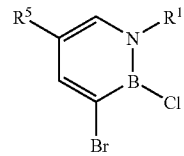

wherein $R^1$ is selected from alkyl having 1-6 carbons, aryl having 1-6 carbons, acyl having 1-6 carbons, or $Si(R^8)_3$, wherein each $R^8$ is independently alkyl having 1-6 carbons, aryl having 1-6 carbons, alkoxy having 1-6 carbons, acyl having 1-6 carbons, or tert-butyloxycarbonyl; and $R^5$ is selected from H, Br, Cl, I, F, —$OR^7$, wherein each $R^7$ is independently alkyl having 1-6 carbons, acyl having 1-6 carbons, or tert-butyloxycarbonyl.

17. The azaborine of claim 16, wherein $R^5$ is Br, Cl, I, or F.
18. The azaborine of claim 16, wherein $R^1$ is —$SiMe_2$t-Bu.

* * * * *